(12) United States Patent
Hedtke et al.

(10) Patent No.: US 8,170,609 B2
(45) Date of Patent: May 1, 2012

(54) PERSONAL VIRTUAL ASSISTANT PROVIDING ADVICE TO A USER REGARDING PHYSIOLOGICAL INFORMATION RECEIVED ABOUT THE USER

(75) Inventors: Paul Hedtke, San Diego, CA (US); Jack Steenstra, San Diego, CA (US); Kirk S Taylor, San Diego, CA (US); Liren Chen, San Diego, CA (US); Richard J Lobovsky, Brooklyn, NY (US)

(73) Assignee: QUALCOMM Incorporated, San Diego, CA (US)

( * ) Notice: Subject to any disclaimer, the term of this patent is extended or adjusted under 35 U.S.C. 154(b) by 1067 days.

(21) Appl. No.: 11/765,983

(22) Filed: Jun. 20, 2007

(65) Prior Publication Data

US 2008/0318624 A1    Dec. 25, 2008

(51) Int. Cl.
*H04M 1/00* (2006.01)
*A61B 5/0245* (2006.01)
*G08B 23/00* (2006.01)

(52) U.S. Cl. .................. 455/556.1; 600/301; 340/573.1

(58) Field of Classification Search ............... 455/556.1; 340/540, 573.1
See application file for complete search history.

(56) References Cited

U.S. PATENT DOCUMENTS

| | | | |
|---|---|---|---|
| 2002/0016719 A1* | 2/2002 | Nemeth et al. ..................... 705/2 |
| 2002/0026223 A1* | 2/2002 | Riff et al. ......................... 607/27 |
| 2002/0123672 A1* | 9/2002 | Christophersom et al. ... 600/300 |
| 2004/0122295 A1* | 6/2004 | Hatlestad et al. .............. 600/300 |
| 2004/0147979 A1* | 7/2004 | Bardy .............................. 607/60 |
| 2005/0209513 A1* | 9/2005 | Heruth et al. .................. 600/301 |
| 2006/0089542 A1 | 4/2006 | Sands |
| 2006/0253006 A1 | 11/2006 | Bardy |
| 2007/0004969 A1 | 1/2007 | Kong et al. |
| 2007/0004970 A1* | 1/2007 | Tice .............................. 600/300 |
| 2008/0139890 A1* | 6/2008 | Craine et al. ................... 600/300 |
| 2008/0246629 A1* | 10/2008 | Tsui et al. .................. 340/573.1 |

FOREIGN PATENT DOCUMENTS

WO    2007044877    4/2007

OTHER PUBLICATIONS

Partial International Search Report—PCT/US08/067513—International Search Authority, European Patent Office—Oct. 14, 2008.
International Search Report—PCT/US08/067513, International Search Authority—European Patent Office—Jan. 19, 2009.
Written Opinion—PCT/US08/067513, International Search Authority—European Patent Office—Jan. 19, 2009.

* cited by examiner

*Primary Examiner* — Nick Corsaro
*Assistant Examiner* — Tangela T. Chambers
(74) *Attorney, Agent, or Firm* — James T. Hagler

(57) ABSTRACT

A personal virtual assistant is provided. The personal virtual assistant includes a medical device and remote station that is connectable via a wireless network to a server containing a control processor and rules engine. The medical device is used to provide physiological information to the remote station. The remote station communicates the physiological information and other related information to the server that monitors the information for a number of reasons, including determining whether the physiological information has a trend. Based on the detrimental trend, the server communicates back to the remote station virtual assistance in the form of advice regarding tips to help facilitate halting or reversing the trend.

49 Claims, 11 Drawing Sheets

PERSONAL VIRTUAL ASSISTANT PROVIDING ADVICE TO A USER REGARDING PHYSIOLOGICAL INFORMATION RECEIVED ABOUT THE USER

CLAIM OF PRIORITY UNDER 35 U.S.C. §119

None.

CLAIM OF PRIORITY UNDER 35 U.S.C. §120

None.

REFERENCE TO CO-PENDING APPLICATIONS FOR PATENT

None.

BACKGROUND

1. Field

The technology of the present application relates generally to a virtual assistant, and more specifically to a personal virtual assistant that receives physiological information regarding a user and provides the user advice relating to the physiological information.

2. Background

Electronic devices are prevalent in most individual's daily lives. For example, a large segment of the population has a cellular telephone. The widespread use of the cellular telephone has made it a convenient platform for many services. Some currently provided services include communication, data transfers, positioning services, such as, for example, GPS services, games, internet access, banking services, and the like.

The aging population also has numerous electronic devices to help monitor and track health information ("generally referred to as "Electronic Medical Devices" or "EMDs"). For example, heart monitors are available to monitor a person's heart rate, variable heart rate, or the like. Moreover, diabetics use blood glucose monitors to track whether they need medication, ingest food or drink, or the like. Unfortunately, most of these devices require the diligence of the person to use and report the findings. For example, self monitoring blood glucose typically involves a person taking readings and creating a log that may be faxed for evaluation.

Recently, there has been a trend to use the electronic devices carried by many people, such as, for example, cellular telephones, to receive data from the EMDs. For example, a person with a pulmonary deficiency may be required to periodically use a blood oxygen monitor to monitor the oxygen content of their blood. The blood oxygen monitor, when used, would transmit the information to the cellular telephone platform, or another type of computing platform, such as a personal computer that is connected to the network. The transmission from the blood oxygen monitor to the cellular telephone may be wireless or via a data port. The information transmitted to the cellular telephone would be transmitted via a wireless network to a remote server. On an alarm condition, for example, if the blood oxygen level dropped below 85%, the remote server (or cellular telephone) would trigger an application of medicine, alert medical personal, such as a primary care provider, or the like.

While the above provides an emergency response, it does not provide any mechanism for intervention prior to a medical emergency. There is therefore a need in the art for a personal virtual assistant that can review information from Electronic Medical Devices and provide feedback and intervention advice prior to an emergency condition.

SUMMARY

Embodiments disclosed herein address the above stated needs by providing systems, methods, and apparatuses for automatically providing virtual assistance to correct detrimental trends of physiological information. The virtual assistance is determined based on the detrimental trend and is designed to halt, offset, or warn the user of the fact.

In one aspect, a personal virtual assistance system is provided. The personal virtual assistance includes a remote station carried by a user and an electronic medical device. The electronic medical device senses physiological information about the user and provides the information to the remote station. The remote station is coupled via a bidirectional communication link to a control processor and rules engine that selects advice based on the information.

In another aspect, a method for automatically providing virtual assistance to a user based on physiological information of the user is provided. The method includes sensing physiological information of the user and transmitting the sensed physiological information of the user to a control processor and rules engine. The control processor and rules engine determine whether the physiological information has a detrimental trend and based on the determination, provide the user with virtual assistance designed to halt or reverse the trend.

DETAILED DESCRIPTION

The technology of the present application will be described with reference to the associated figures. The technology will be described with reference to particular exemplary embodiments. The word "exemplary" is used herein to mean "serving as an example, instance, or illustration." Any embodiment described herein as "exemplary" is not necessarily to be construed as preferred or advantageous over other embodiments. Moreover, any embodiments described herein should be considered exemplary unless otherwise indicated.

Figure 1:
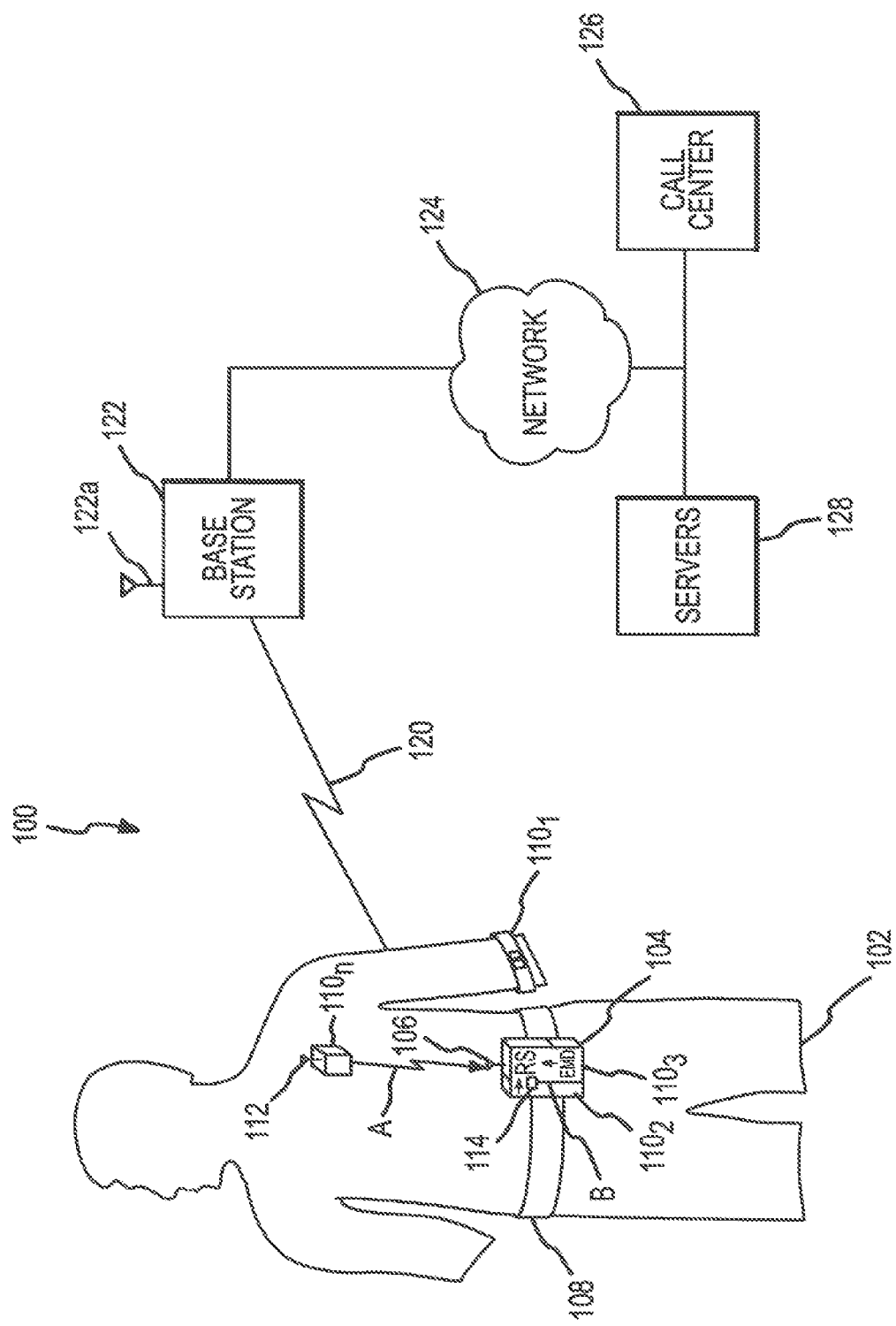
FIG. 1 is a block diagram illustration of a wireless communications system of an exemplary embodiment of the disclosure.

Referring first to FIG. 1, a personal virtual assistant (PVA) system 100 constructed using the technology of the present application is illustrated. In this exemplary system 100, a PVA user 102 is provided. PVA user 102 would have a remote station 104. Remote station 104 would have at least one radio frequency antenna 106, but may have multiple antennas. Frequently, remote station 104 will transmit and receive radio frequency signals over multiple operational frequencies that may require either multiple antennas or a single antenna that operates over the necessary frequencies. Remote station 104 may consist of any number of devices such as, for example, a wireless computer, a portable digital assistant (such as a BLACKBERRY®, from Research in Motion, Ltd), a cellular telephone, or the like. Remote station 104 may be held by PVA user 102, but would typically be clipped to the user via a conventional device holder on a belt 108 or the like. Remote station 104 is described generally as a compact device for mobility, but one of ordinary skill in the art will recognize that remote station 104 also may be a special processor uniquely designed for the above system, a desktop computer, a laptop computer, a handheld computer, as well as other processors.

PVA user 102 also has one or more EMDs $110_{1-n}$. EMDs $110_{1-n}$ may include, by way of non-limiting example, a pulse meter $110_1$, a blood glucose meter $110_2$, a oxygen meter $110_3$, a cardio monitor $110_n$, etc. EMDs $110_{1-n}$ may be separate from remote station 104, such as pulse meter $110_1$ and cardio monitor $110_n$, or integrated or removably attached to remote station 104, such as, for example, blood glucose meter $110_2$ may be integrated with remote station 104 and oxygen meter $110_3$ may be removable attached. EMDs $110_{1-n}$ provide information and data regarding the physiological conditions of PVA user 102. The data transmitted between EMDs $110_{1-n}$ and remote station 104 may be via a wireless data link A between antenna 112 on EMD 110 and antenna 106 or a wired data link B such as over cable 114. Wireless data link may be a low power connection as the distances the signal needs to travel are typically smaller and the interference is less. Low power transmission is typically a lower radiating signal, which is beneficial for PVA user 102. While several EMDs $110_{1-n}$ are provided in FIG. 1, the technology of the present invention will be described with reference to only a limited number of exemplary EMDs for brevity and convenience.

Remote station 104 is connected via a wireless communication network 120 to a base station 122. Base station 122 has an antenna 122a. Antenna 106 and antenna 122a can transmit and receive respective radio frequency signals to allow data transfer between remote station 104 and base station 122. Base station 122 is interconnected to one or more networks 124. Although network 124 may be several networks, network 124 will be described as a single network for convenience. One or more call centers 126, which may be medical assistance centers, and servers 128 are interconnected to base station 122 through network 124. Network 124 may be a LAN, WAN, WLAN, PAN using any wired or wireless network technology. System 100 is shown with a single PVA user 102 and a single base station 122, but it is envisioned that system 100 would support multiple PVA users 102 as well as multiple base stations 122. In these instances, it may be beneficial to incorporate security measures in the system, such as, for example, biometric information, passwords, cellular identification signals, or the like, or a combination thereof to secure the medical information. See U.S. patent application Ser. No. 11/626,789, filed Jan. 24, 2007, and titled MOBILE PHONE BASED AUTHENTICATION AND AUTHORIZATION SYSTEM AND PROCESS TO MANAGE SENSITIVE INDIVIDUAL RECORDS.

Remote station 104 communicates with base station 122 using a conventional protocol, such as CDMA or the like, although any analog or digital protocol is acceptable. Moreover, while described using a cellular network for communication and data transfer between remote station 104 and base station 122, other wireless or wired networks are possible.

Figure 2:
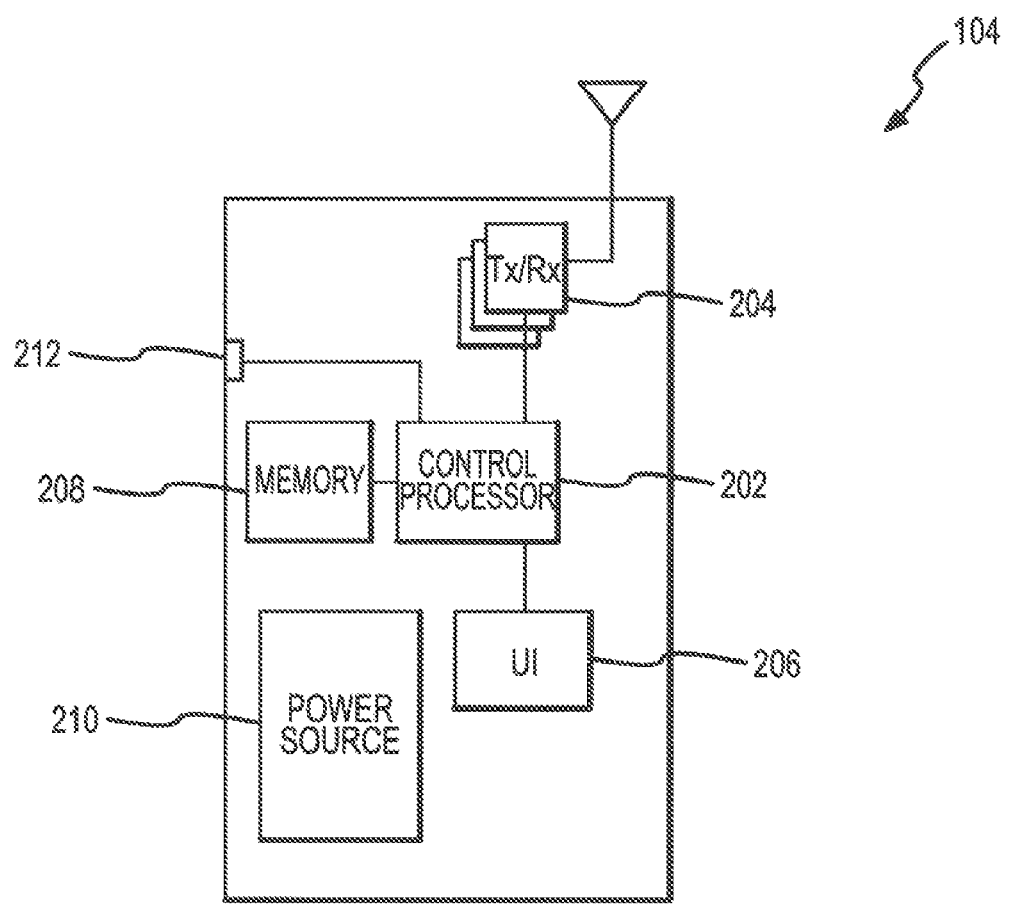
FIG. 2 is a block diagram illustration of a remote station of an exemplary embodiment.

Referring now to FIG. 2, an exemplary embodiment of remote station 104 is shown in more detail. Remote station 104 includes several components including a control processor 202. Control processor 202 controls the major functions of remote station 104 including providing computing functionality to process the inputs and/or data required for the operation of remote station 104. Transmit/receive circuitry 204 is connected to control processor 202 and antenna(s) 106. Transmit/receive circuitry 204 may be one or more actual circuits and may work over various protocols and wavelengths. Transmit/receive circuitry 204 functions typical of such components as used in wireless communications, such as modulating signals received from the control processor 202 that are to be transmitted from antenna 106, and demodulating signals received at antenna 106. The demodulated signal is provided to control processor 202.

Remote station 104 includes a user interface 206. User interface 206 may comprise a user interface typical of a cellular phone or typical of the wireless device, such as, for example, a keyboard, alphanumeric pad, mouse, track ball, touch screen, voice recognition, microphones, speakers, data ports, input ports, or the like. The PVA user 102 access, receives, and transmits information via user interface 206.

Remote station 104 includes a memory 208 connected to control processor 202. Memory 208 may store data and processing instructions necessary or convenient for operation of remote station 104. Memory 208 may include volatile and/or nonvolatile memory on any suitable media.

Remote station 104 includes a power source 210. Power source 210 may be any conventional power source and is typically a battery pack. Remote station 104 also may include a data port 212 connected to control processor 202. While not illustrated in FIG. 2, remote station 104 includes additional components and connections, such as, for example, cables, interfaces, circuit boards, and the like conventional in such devices for operation.

Figure 3:
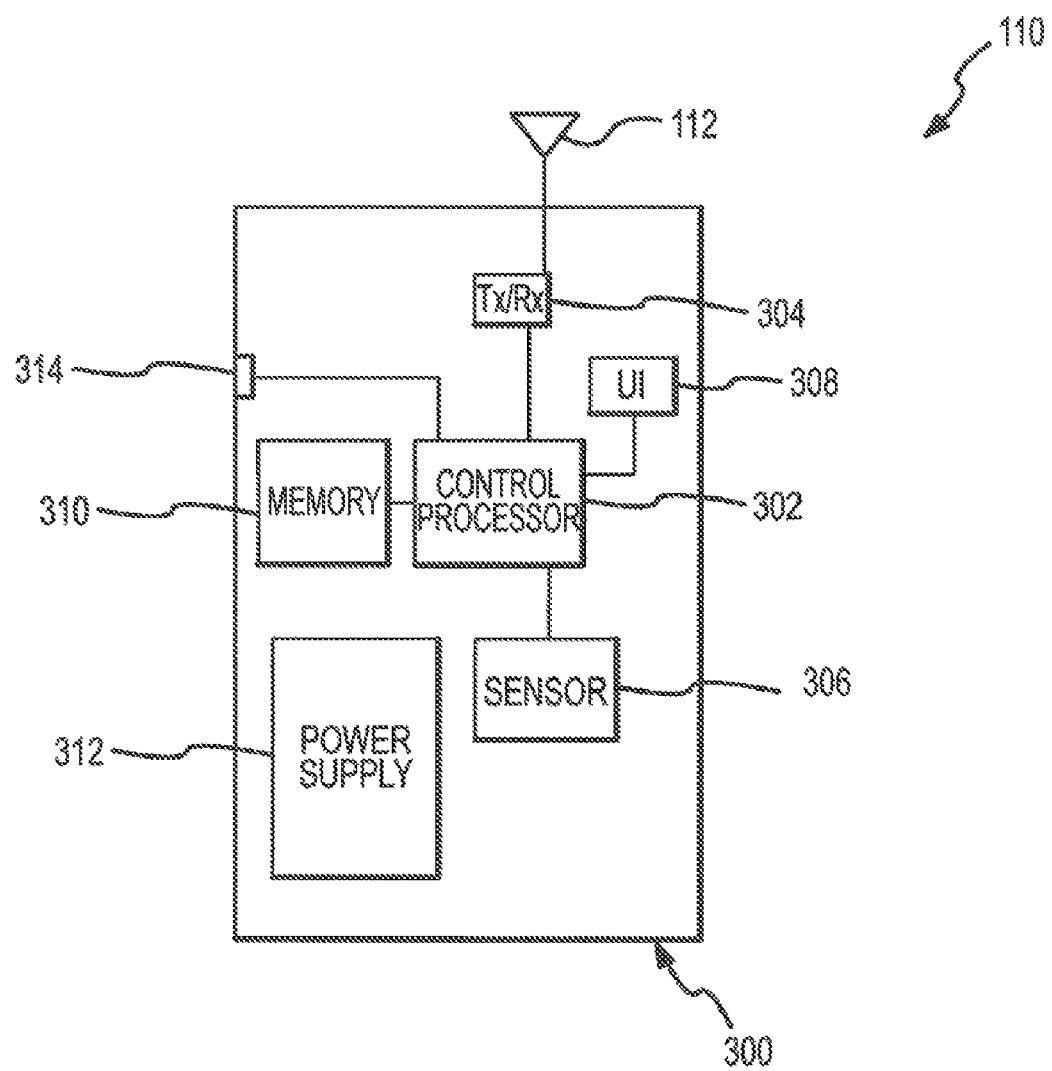
FIG. 3 is a block diagram illustration of an electrical medical device of an exemplary embodiment.

Referring now to FIG. 3, an exemplary EMD 110 is shown in more detail. EMD 110 has a medical device electronics package 300. Medical device electronics package 300 includes the electronics necessary for EMD 110 to perform its intended function. EMD 110 also includes a control processor 302 that could incorporate package 300. Control processor 302 controls the major functions of EMD 110 including providing computing functionality to process the inputs and/or data required for the operation of EMD 110. Transmit/receive circuitry 304 is connected to control processor 302 and antenna(s) 112. Transmit/receive circuitry 304 may be one or more actual circuits and may work over various protocols and wavelengths. Transmit/receive circuitry 304 functions typical of such components as used in wireless communications, such as modulating signals received from the control processor 302 that are to be transmitted from antenna 112, and demodulating signals received at antenna 112. The demodulated signal is provided to control processor 302.

EMD 110 includes a sensor 306. Sensor 306 may comprise a sensor typical for the physiological information desired, such as, for example, an infrared sensor, a pulse sensor, a pulse/oxygen sensor, an oxygen monitor, or the like. Sensor 306 should be construed broadly to include medical input ports also. Such ports may include, for example, a breath tube, a blood specimen port, or the like. The physiological information is received by EMD 110 via sensor 306 and processed as necessary by medical device electronics package.

EMD 110 also may include a user interface 308. User interface 308 may comprise a user interface typical of a cellular phone or typical of the wireless device, such as, for example, a keyboard, alphanumeric pad, mouse, track ball, touch screen, voice recognition, microphones, speakers, or the like. The PVA user 102 access, receives, and transmits information via user interface 308.

EMD 110 includes a memory 310 connected to control processor 302. Memory 310 may store data and processing instructions necessary or convenient for operation of EMD 110. Memory 308 may include volatile and/or nonvolatile memory on any suitable media.

EMD 110 includes a power source 312. Power source 312 may be any conventional power source and is typically a battery pack. While not illustrated in FIG. 2, EMD 110 includes additional components and connections, such as, for example, cables, interfaces, circuit boards, and the like conventional in such devices for operation.

FIG. 3 shows as exemplary EMD 110 remote from remote station 104. Thus, data from EMD 110 to remote station 104 may be transmitted via a wireless connection between antenna 112 and 106, which may be a low power signal to reduce radiation exposure to PVA user 102. Alternatively, control processor 302 may be connected to a data port 314 that connects to data port 212 in remote station 104 to provide a wired data link. Also, some EMDs 110 may be integrated into remote station or plugged into remote station (such as EMDs $110_2$ and $110_3$ in FIG. 1). When integrated or otherwise connected to remote station 104, EMD 110 may share certain portions and functions. For example, the power supply, UI, memory, and the like may be shared resources.

Figure 4:
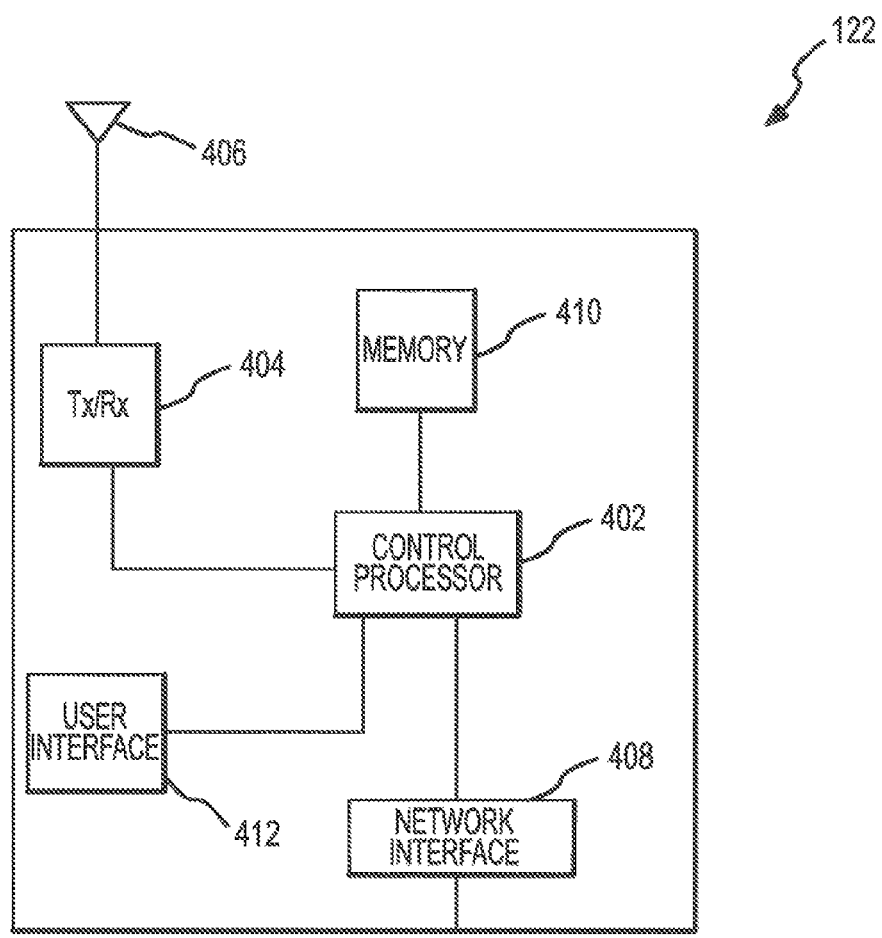
FIG. 4 is a block diagram illustration of a base station of an exemplary embodiment.

FIG. 4 shows an exemplary base station 122. Base station 122 includes a control processor 402 connected to transmit/receive circuitry 404, which is connected to antenna 406. Wireless communication between antenna 106 and 406 may be via CDMA protocols or any analog/digital wireless protocol. Similar to antenna 106, antenna 406 may include different operating frequencies or multiple antennas to accommodate multiple operating frequencies. Control processor 402 further includes a network interface 408 to connect base station 122 to network 124 (FIG. 1). Base station 122 further includes a memory 410 connected to control processor 402, and may store processing instructions for execution. Memory 410 also may store data necessary or convenient for operation of base station 122. Memory 410 may be volatile and/or nonvolatile on any acceptable media. Base station 122 may include a user interface 412 to allow access to network personally to access base station 122.

Figure 5:
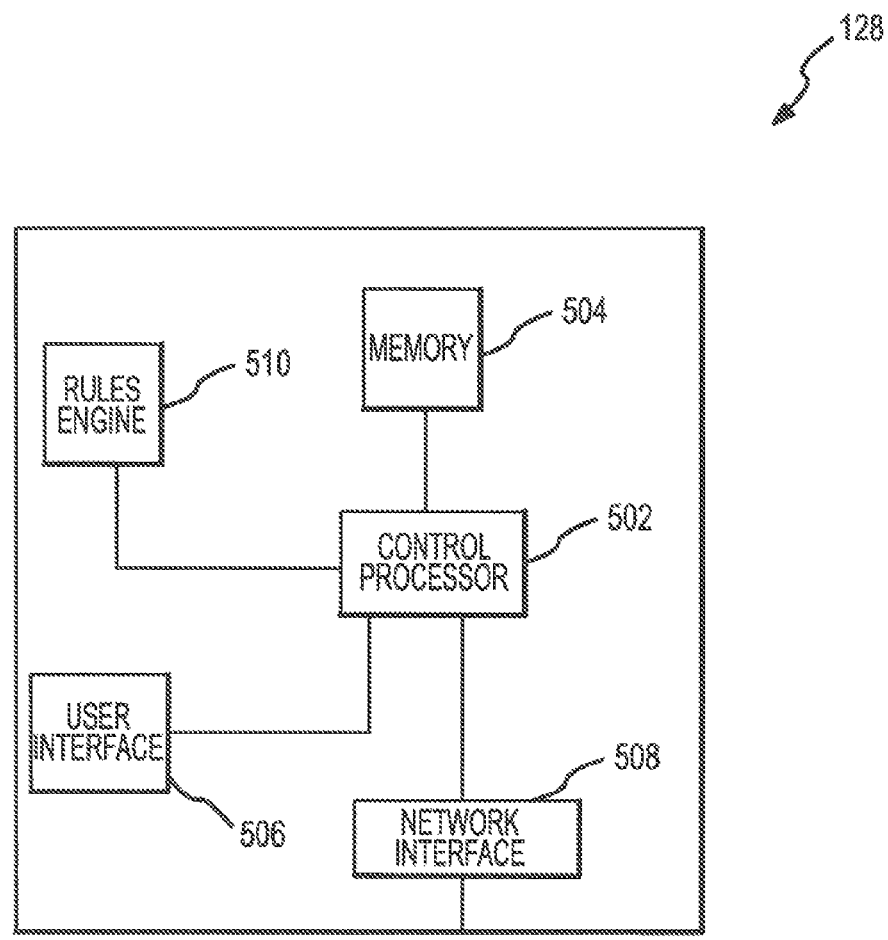
FIG. 5 is a block diagram illustration of a server of an exemplary embodiment.

FIG. 5 is a block diagram illustration of server 128 of an exemplary embodiment. Server 128 includes a control processor 502 connected to a memory 504, a user interface 506, a network interface 508, and a rules engine 510. Memory 504 may store processing instructions to be executed by control processor 502 as well as data necessary or convenient for the operation of server 128. Memory 504 may be volatile and/or nonvolatile. Use interface 506 provides an interface for personnel to interface with server 128, such as, for example network administrators, medical care providers, call center personnel or the like. Rules engine 510 contains predefined or generated advice, alerts, alarms, or the like relating to physiological conditions monitored by EMDs 110, as will be explained in further detail below. The generated advice, alerts, alarms, or the like, may include, for example, tips to reverse a detrimental trend in the physiological condition being monitored (for example, rising pulse rate may result in a tip such as "sit down and rest for a moment"), an alert sent to a care provider or medical personnel (for example, if after providing a series of tips the tend remains, a care provider may be alerted to check on PVA user 102), or an alarm (for example, dispatching an emergency medical team on a dangerous condition being detected). While shown as a separate component, rules engine 510 may be integrated with control processor 502.

Figure 8:
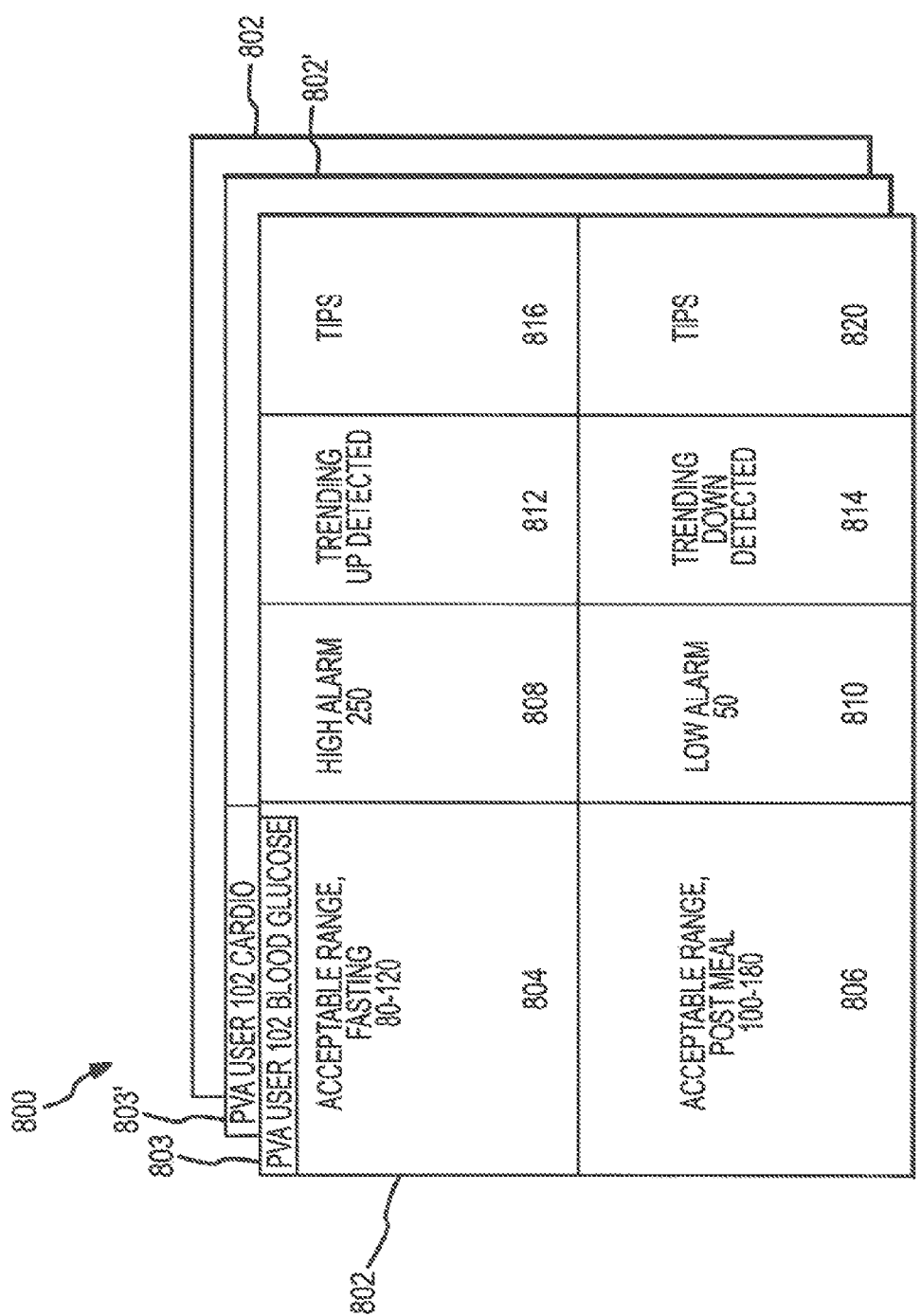
FIG. 8 is block diagram of a memory structure of an exemplary embodiment.

Rules engine 510 may take many different forms, but one exemplary embodiment includes a database 800, see FIG. 8, such as, for example, an Excel spreadsheet. The database would include a PVA user 102 field that stores information relating to PVA user 102 and may be tailored specifically to PVA user 102. Rule engine would have a number of rule entries that are associated with triggering events as will be described further below.

Figure 6:
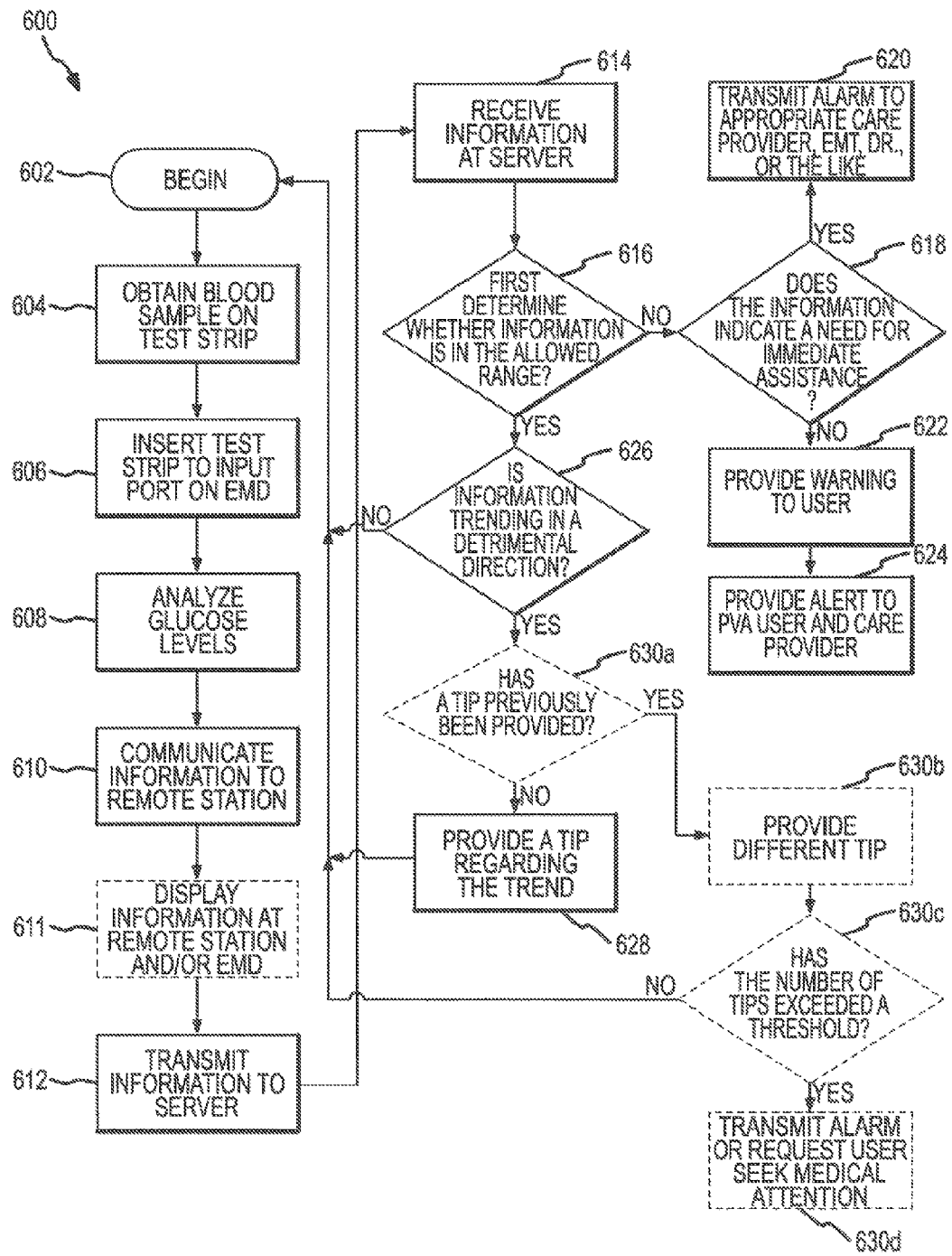
FIG. 6 is a flow chart diagram illustrating the operational steps for automatically providing virtual assistance of an exemplary embodiment.

Referring now to FIG. 6, operational steps for using the PVA system 100 to provide information, tips, advice or the like are now described for an exemplary embodiment. It is noted, at the outset, that the operational steps described in any of the exemplary embodiments are described to provide examples and discussion. The operations described may be performed in numerous different sequences other than the illustrated sequences. Further, operations described in a single operational step may actually be performed in a number of different steps. Additionally, one or more operational steps discussed in the exemplary embodiments may be combined. Moreover, operational steps described as occurring at one processor may be performed at other processors. It is, therefore, to be understood that the operational steps illustrated in the flow charts and diagrams may be subject to numerous different modifications as will be readily apparent to one of skill in the art on reading the present disclosure.

In FIG. 6, the operational steps will be described with reference to a blood test relating to glucose levels, in particular, flow chart 600 relates to the self-monitoring of blood glucose (SMBG test). The operation begins at step 602. First, PVA user 102 will obtain a drop of blood on a test strip, step 604. A drop of blood or sample is typically obtained by a finger prick. Next, the test strip is inserted into a strip input on EMD 110, step 606. The EMD analyzes the glucose level of the blood sample, step 608. In some cases, the EMD needs to be powered to perform the analysis, in others, inserting the strip into the strip input may activate the EMD. The glucose information is communicated to remote station 104, step 610. Remote station 104 and or EMD 110 optionally displays the information on user interface 206 and/or user interface 308 respectively, step 611. The information may be communicated via a wireless connection, such as a Bluetooth data connection or a wired connection, such as a serial port, universal serial bus (USB) cable or the like. If the EMD is integrated or plugged into the remote station 104, the data transfer may be via ribbon cable, bus connections, such as PCI buses, or the like.

The following description relates to the case where the majority of the information processing is performed at server 128, but it can be appreciated that the processing described as occurring at server 128 may be done by remote station 104 instead of server 128 or a combination thereof. The information, in this case blood glucose levels, are transmitted by remote station 104 to server 128 via base station 122 and network 124, step 612. Sever 128 receives the information, step 614, and first determines whether the information is within the allowable range, step 616. If it is determined the information is outside the allowable range, it is next determined if the information requires immediate medical response, EMT response, medicine application, or the like, step 618. If immediate medical response is necessary, appropriate information is transmitted to, for example, a care provider or the like, step 620. If immediate medical response is not necessary, by the information is outside the allowable range, rules engine 510 provides an alert to the user to contact medical personnel as soon as possible, step 622. Such a warning may request more frequent monitoring of the physiological condition and if such more frequent monitoring is not performed, an alert to a care provider may be provided, step 624.

If the information is within the allowable, preset range, it is next determined whether the information is trending in a detrimental direction, step 626. If the information is not trending in a detrimental direction, control returns to step 602. Trending in a detrimental direction may be a gradual change over a relatively long time, or a relatively abrupt change over a relatively short time. In the case of blood sugar, increasing glucose levels and decreasing glucose levels may indicate a detrimental trend. If a detrimental tend is detected, the rules engine provides a first tip for countering the trend, step 628. After the tip is transmitted or provided to PVA user 102, control would go back to the beginning, step 602. For example, increasing glucose levels may prompt a tip, such as, for example, "take your insulin shot." A decreasing glucose level may prompt a tip such as, for example, "drink a glass of juice." The tip may be a single pre-defined tip for a given rule violation or may be one of a random sampling plurality of appropriate first tips. Optionally, at step 630a shown in phantom, the system may check to determine whether a tip has previously been provided. If a tip has previously been provided, rules engine may provide a second tip, step 630b, different than first or at least last tip. For example, if the first tip was "take your insulin shot," the second tip may be "take your diabetes pill." While numerous tips may be provided, after a predetermined number of tips, optionally, the PVA user 102 may determine a threshold, step 630c, causing a tip requesting PVA user 102 to seek medical advice as the tips are not working as expected or an alarm may be transmitted, step 630d. While described as information tending in a detrimental direction, it should be appreciated the above described system may involve recording and rewarding information trending in a healthy direction. For example, if particular activities lower a user's blood pressure, the system may reward the healthy trend and provide a health tip relating to the healthy trend, such as, for example, "walking 1 mile a day has lowered your blood pressure—keep it up."

Instead of basing the second, third, fourth, etc. tips based on previously provided tips, the system could be established with numerous thresholds. Thus, a first tip from a first group of tips may be provided for a first range of glucose levels. A second tip from a second group of tips may be provided for a second range of glucose levels, etc. Moreover, the rules engine could be established for a pre meal and post meal test.

Figure 10:
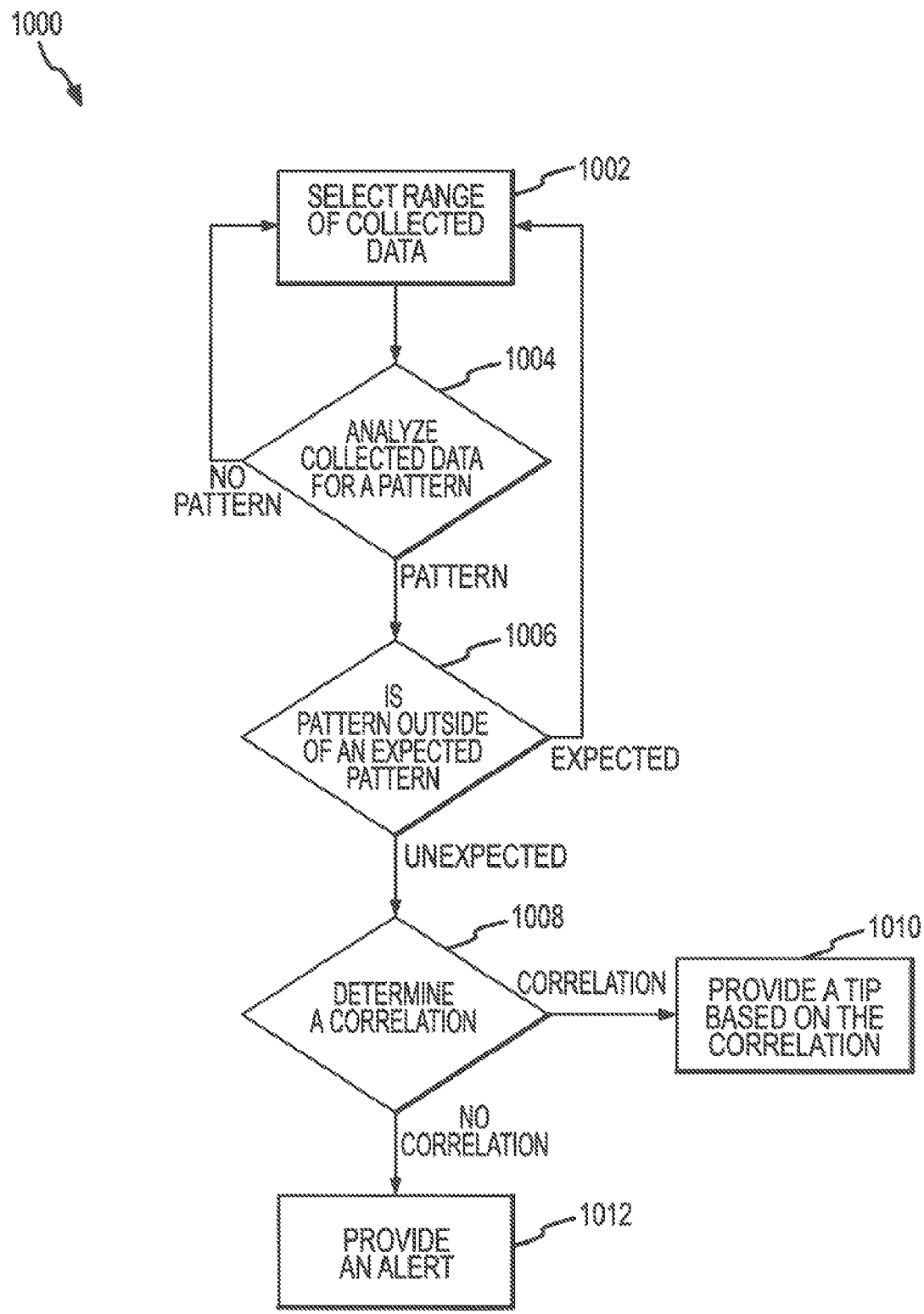
FIG. 10 is a flow chart diagram illustrating the operational steps of recognizing a pattern over a selected period of an exemplary embodiment.

In addition to threshold-triggered alerting and trending, the virtual assistant system is also capable of performing pattern recognition. For example, by analyzing the blood glucose levels over a multi-day period, our system might be able to detect that a particular user's glucose reading tends to become too high, or too low at certain time of the day. This maybe a result of the user's diet, exercise or work load. Using the rule engine, the system would then be able to deliver recommendations for diet, exercise and work load in order to better manage the user's health condition. For example, referring to flowchart 1000 of FIG. 10, an exemplary pattern recognition process is provided. First, processor 502 selects a range of collected data, step 1002. As described above, the system may analyze blood glucose levels over several days, weeks, months, or the like. Next, processor 502 would analyze the collected data to determine whether a pattern in the data exists, step 1004. If no pattern is identified, the system reverts back to step 1002. If a pattern is identified, processor 502 would determine whether the pattern is outside of an expected pattern, step 1006. If its an expected pattern, control return to step 1002. If the pattern is not an expected pattern, processor 502 looks to determine one or more correlation between the pattern and recorded events (which are explained further below), step 1008. As mentioned, the blood glucose level may change daily at 3:00 PM due to a trip to the gym. If a correlation is determined, a tip may be sent to the user, for example, at 2:45 PM a tip just prior to the exercise session may suggest that the user drink a glass of juice, step 1010. If a correlation is not determined, a tip may be sent to the user warning the user of the pattern and alerting them to be extra careful or the like, step 1012. Alternatively or in conjunction with the alert to the user in step 1012, the pattern not having a corollary event may send an alert to care givers or the like to determine if a corollary event is present but not identified in the rules engine. One potential benefit for the historical analysis is to capture information that may not be statistically significant as a one time event, but over several days, weeks, months or the like presents a pattern that should be identified.

As identified above, the technology described in the present application should be provided with a basic input/output system (BIOS) whether at the EMDs 110 or the remote station 104, or a separate device, such as a networked computer, relating to other information relevant to the user's physiological data. The input information could be events the user, medical personnel, or the like expect to influence the measured physiological data. Using this information, and correlating the information to the EMD based data provides additional information relating to the user's condition and allows more finally tuned advise that is most likely relevant to the user's condition. For example, the system would collect the user's diet information (most likely through manual input from a conventional telephone, a BIOS associated with the remote station or EDM, a website, or the like), user's medication information (this can be done through manual input similar to the above or automatic integration with an existing medicine management system) and the user's exercise information (again, can be collected manually, or through sensors, such as built-in accelerometer in the EMDs, the remote station, a separate cellular phone, or the like). After the information are collected and stored in the database, the virtual assistant would then match the diet, exercise and medication information with the user's physiological conditions and make personalized recommendations using the rule engine. For example, in flow chart 600 an optional (such as between step and step 628) may be include that determines if the detected trend corresponds to an event. For example, an elevated heart rate of the user may be detected. However, it the system may have additional input indicating the user is jogging. Thus, the increasing trend of the heart rate may not justify a tip in view of the additional information.

The above system is ideally performed on a real time or near real time basis. However, in some situations, such as network failures, out of coverage areas, the various information may need to be cached prior to transmissions. When the system is not functioning, an alert should be provided to the PVA user 102.

Figure 7:
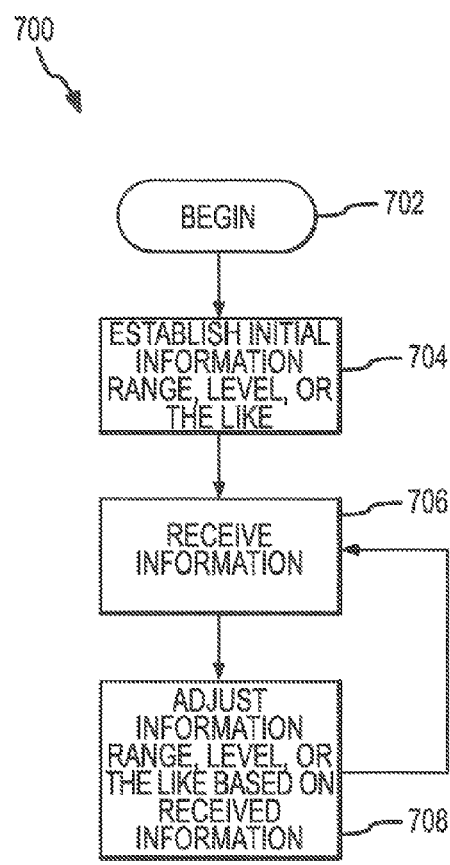
FIG. 7 is a flow chart diagram illustrating the operational steps of altering information ranges of an exemplary embodiment.

Flow chart 700 provides a first determination whether the information is within an allowable range. For example, for a pulse monitor, the first determination of whether the pulse is in an allowable range may be pre-set to a default level, such as, 60-100 beats per minute. While this setting is acceptable, over time the rules engine should become tailored to the specific PVA user 102 as described by PVA user 102's physiological conditions as shown by FIG. 7. Additionally, the PVA user 102 or the PVA user 102's health care provider may tailor settings specific to the PVA user 102. The process begins at step 702. Establish initial information ranges, levels, or the like, step 704. The initial information could be present to a statistical "normal" range or preset by a care provider. Rules engine receives information relating to the resting pulse rate of PVA user 102, step 706. The information range, level, or the like is adjusted based on the information relating to, for example, the resting pulse rate, step 708. If PVA user 102's resting pulse rate is typically 70-72 beats per minute, over time, the allowable threshold for pulse should change from the default level of 60-100 beats per minute to one more user specific range of, for example, 65-75 beats per minute. To avoid false high readings, a pulse monitor may have a resting setting, a working setting, and an exercise setting, etc. The adjustment can be accomplished by any of several methods, one such example being a weighted average.

Referring now to FIG. 8, a possible database 800 usable by rules engine 510 is provided. Exemplary database 800 is provided with particular fields and information to provide an organizational structure. However, one of ordinary skill in the art would recognize other and different fields and information are possible without deviating from the spirit and scope of the technology described in this application. Moreover, numerous organization devices and methods are possible. Database 800 includes several folders 802. Each folder 802 would be associated with a particular PVA user 102. Folder 802 also may be identified by PVA user 102 and particular EMD 110 in an identification field 803. For example, a PVA user 102 may have a first folder 802 for a blood glucose EMD and a second folder 802' for a cardio monitor EMD, etc. First folder 802 will be described for a SMBG EMD. First folder 802 has an acceptable range, fasting field 804 and an acceptable range, post meal field 806. As shown, fasting field 804 may be set to a default acceptable level of 80-120. Post meal field 806 may be set to a default acceptable level of 100-180. Folder 802 also may have a high alarm setting 808, such as, for example, greater than 250, and a low alarm setting 810, such as, for example, less than 50. Folder 802 also has a trending up field 812 and a trending down filed 814. Trending up field 812 and trending down filed 814 may be segregated into several fields to provide first, second, third thresholds, etc. Linked to trending up field 812 is a tip field 816. Linked to trending down field 814 is another tip field 820. The number of tips fields and the number of tips in each field depends on the fine tuning of the monitoring, the type of monitor, the type of physiological condition, and the like. Database 800 also may contain a schedule field 818. Schedule field would trigger a tip to the PVA user to perform the requested physiological monitoring, such as the SMBG test if require. Always on monitors would not require such a field, but may have a field to alert PVA user when information is not being provided by the EMD.

Moreover, database 800 is not a static structure. As explained above, the fields may have a self learning component to adjust the ranges for supplying tips. In the specific example of the heart rates provided, the initial field may default to providing a tip, such as, "please rest for a moment" when the PVA user's heart rate trends towards the high alarm of 100. However, if the PVA user's heart rate is determined to be normally in the 65 to 75 bpm range, the field may be adjusted to provide the tip "please rest for a moment" when the PVA user's heart rate trends towards 75 bpm. The care giver of course could tailor the fields and alarm/tip settings for the individual user or simply use the default settings and allow the system to self learn the individual.

As part of the periodic monitoring for patterns, the data regarding the monitored physiological data and provided tips may be stored in, for example, server memory 504. Periodically, the physiological data and tips are reviewed by a service provider, such as, for example, a nurse, a doctor, a nurse practitioner, or the like. This service provider would look for an identify patterns not previously detected by the processor as described in relation to FIG. 10. Moreover, the service provider may review and adjust the ranges for the particular PVA user to augment, supplant, or instead of the self learning procedure, one example of which is provided above.

Figure 11:
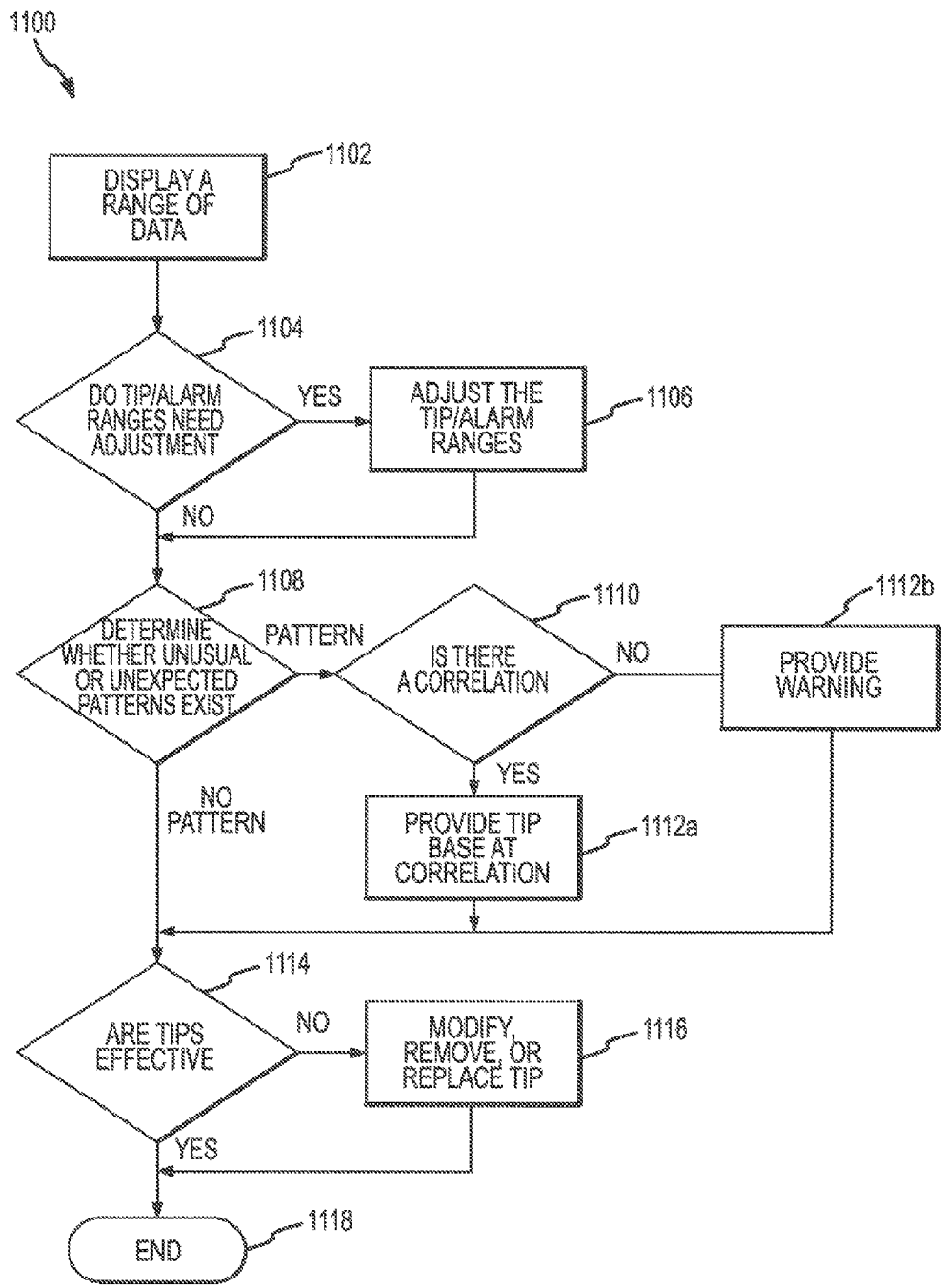
FIG. 11 is a process flow diagram illustrating a service provider method for performing a review process in accordance with an embodiment.

Referring to FIG. 11, a flowchart 1100 exemplary of a review process performed by the service provider is shown. First, the service provide would display a range of data for a PVA user, step 1102. The range of data would include the physiological data monitored over a period of time and the associated tips that may have been provided to the PVA user. Using the displayed data, the service provider may determine the tip/alarm ranges or the like need to be adjusted, step 1104. If so, the service provider would adjust the tip/alarm ranges, step 1106. Using the displayed data, the service provider may determine an unusual pattern or unexpected pattern exists in the data, step 1108. If an unusual or unexpected pattern is determined, the service provider would determine whether a correlation in the PVA user's data exists as described in an exemplary embodiment above, step 1110. The service provider may provide a tip, step 1112a, if a correlation exists, or a warning, step 1112b, if no correlation exists, step 1112. Using the displayed data, the service provider may determine the effectiveness of one or more tips, step 1114. If the tip is ineffective, the tip may be modified, removed, or replaced, step 1116. For example, if a person is having their heart rate monitored, an upward trend in the beats per minute may cause a first tip to the PVA user of "rest for a moment." On reviewing the data, the service provider may note that the first tip is ineffective at reversing the trend. The tip may be modified, such as, for example, instead of "rest for a moment" to "rest for at least 10 minutes." Alternatively, the tip may be replaced with a new tip, which may be, for example, "increase your oxygen supply" if the PVA user is using oxygen. If the tip is determined to effectively reverse the trend, or after the tip is modified, removed, or replaced, the service provider review may end or be re-performed for other tips, EMD, or the like, step 1118. While described as being performed by a service provider, a control processor also could determine whether particular tips are having the desired effect. For example, if after 3 successive provisions of the first tip, the second tip is always provided, the system could automatically modify, replace, or remove the first tip. If automatic calibration is elected, the first step 1102 would be replaced with monitoring a range of data as it would not need to be physically displayed.

Tip field may comprise a single tip, such as, for example, take an insulin shot, or a plurality of rules and tips. The tips may be segregated into several fields corresponding to first, second, etc. thresholds. Thus, a first tip may be: take an insulin shot, when the first threshold is reached. A second tip may be: take a diabetes pill, when the second threshold is reached, etc. Alternatively, the upwards trend may be tracked and a different tips may be provided until the trend is reversed or corrected. After a predetermined threshold or a predetermined number of tips, the tip may be to contact medical personnel or the PVA may escalate to medical personnel who will contact the PVA user.

Figure 9:
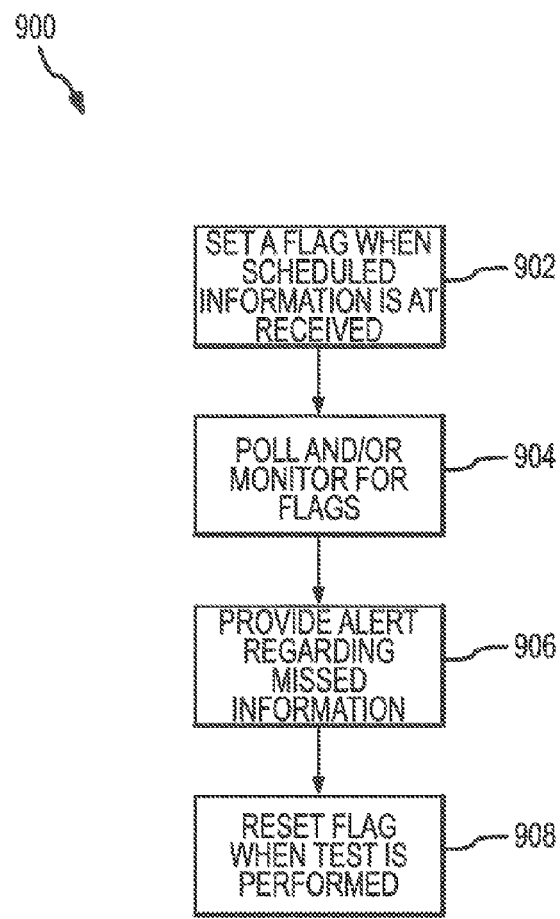
FIG. 9 is a flow chart diagram illustrating the operational steps of providing an alert when scheduled information is not received.

Referring to FIG. 9 is an exemplary embodiment of a physiological test reminder. Rules engine 510 sets a flag when a scheduled test is missed, step 902. Central processor 502 periodically monitors or polls database 800 for flags, step 904. When it is determined a schedule monitoring event was missed, central processor would send an alert remote station 104, step 906. The alert may be a text message, email, pre-recorded phone message, graphical icon or other visual or audio alert. When the test is performed, and the information sent to rules engine 510, the flag would be reset, step 908.

While the above is described with certain features and actions taking place at the remote station and/or server, such locations of features and actions is largely a matter of convenience. Many of the functions, tip generations, etc., can be performed at either location.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in the remote station, Electronic medical device, a server, or a combination thereof. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A personal virtual assistant system, comprising:
a remote station configured to be carried by a user;
an electronic medical device to sense physiological information about the user, the electronic medical device coupled to the remote station;
a control processor coupled to the remote station via a bidirectional communication link; and
a rules engine coupled to the control processor,
wherein the control processor and rules engine use a combination of user input data and the sensed physiological information to determine whether a medical trend exists and, based on the determination of the medical trend, automatically provide advice relating to the medical trend,
wherein the control processor and rules engine are configured to determine whether advice relating to the medical trend was previously provided and if it is determined previous advice was provided and that the trend persists, providing different advice relating to the medical trend based on a combination of previously provided advice, the medical trend, and the user input data, and
wherein the user input data includes diet information.

2. The personal virtual assistant system according to claim 1, wherein the medical trend is a detrimental medical trend and the advice is to counter the detrimental medical trend.

3. The personal virtual assistant system according to claim 1, wherein the medical trend is a healthy medical trend and the advice is to promote the healthy medical trend.

4. The personal virtual assistant system according to claim 1, wherein the system operates in at least one of real time or near real time.

5. The personal virtual assistant system according to claim 1, wherein the system caches the physiological information.

6. The personal virtual assistant system according to claim 1, wherein the control processor and the rules engine are located in a server remote from the remote station.

7. The personal virtual assistant system according to claim 6, wherein server is coupled to the remote station via a base station and a wireless network.

8. The personal virtual assistant system according to claim 7, wherein the server is coupled to the remote station via a wired network.

9. The personal virtual assistant system according to claim 1, wherein the electronic medical device is coupled to the remote station via a wireless data link.

10. The personal virtual assistant system according to claim 9, wherein the wireless data link is a low power connection.

11. The personal virtual assistant system according to claim 1, wherein the electronic medical device is integrated into the remote station.

12. The personal virtual assistant system according to claim 1, wherein the electronic medical device is removably connected to the remote station.

13. The personal virtual assistant system according to claim 1, wherein the electronic medical device is connected to the remote station via a wired data link.

14. The personal virtual assistant system according to claim 13, wherein the wired data link comprises a universal serial bus (USB) data port.

15. The personal virtual assistant system according to claim 1, wherein the control processor and rules engine also use the sensed physiological information to determine whether an immediate medical need exists and, based on the determination of the immediate medical need, automatically provides an alert to emergency medical personnel.

16. The personal virtual assistant system according to claim 1, wherein the electronic medical device comprises a plurality of electronic medical devices.

17. The personal virtual assistant system according to claim 1, wherein the electronic medical device is selected from a group of medical devices consisting of: a blood glucose monitor, a pulse monitor, a cardio monitor, a variable heart rate monitor, a blood oxygen monitor, an oxygen monitor, or a blood pressure monitor.

18. The personal virtual assistant according to claim 1, wherein the rules engine uses a plurality of information relating to the user, the plurality of information selected from the group of information consisting of: dietary, activity, emotional mood, stress, or schedule information.

19. A method for automatically providing virtual assistance to a user based on physiological information of the user, the steps comprising:
obtaining user input data comprising diet information;
obtaining physiological information of the user with an electronic medical device;
transmitting the obtained user input data and the obtained physiological information of the user to a control processor and rules engine;
determining by the control processor and rules engine whether the combination of physiological information and user input data identify a trend; and
if it is determined that the trend exists, automatically providing the user with virtual assistance from the control processor and rules engine based on the trend, wherein the step of automatically providing the user with virtual assistance comprises the steps of:
determining whether virtual assistance was previously provided based on the trend; and
if it is determined previous virtual assistance was provided, providing different virtual assistance that takes into account previous virtual assistance, the trend, and the user input data.

20. The method according to claim 19, wherein the determined trend is a detrimental trend and the virtual assistance relates to countering the detrimental trend.

21. The method according to claim 19, wherein the determined trend is a beneficial trend and the virtual assistance relates to promoting the beneficial trend.

22. The method according to claim 19, wherein the virtual assistance is provided in at least one of real time or near real time.

23. The method according to claim 19, wherein the step of transmitting the obtained physiological information of the user further comprises:
transmitting the obtained physiological information to a remote station.

24. The method according to claim 23, wherein the step of transmitting the obtained physiological information to the remote station comprises using a low power transmission.

25. The method according to claim 19, wherein the step of transmitting the obtained physiological information to the control processor and the rules engine comprises using a wireless communication path to a server.

26. The method according to claim 19, further comprising the step of:
determining whether the amount of different virtual assistance exceeds a predefined amount, and
if the amount of different virtual assistance exceeds the predefined amount, providing an alarm to emergency medical personnel.

27. The method according to claim 19, wherein the step of determining by the control processor and rules engine whether the physiological information has a trend further comprises:
establishing a plurality of ranges relating to the trend;
determining which of the plurality of ranges the trend resides in; and
providing virtual assistance to the user based on the range the trend resides in.

28. The method according to claim 27, wherein the plurality of ranges are preset.

29. The method according to claim 28, wherein the plurality of ranges are preset by at least one of a medical provider or a caregiver.

30. The method according to claim 27, wherein the plurality of ranges are adjusted based on sensed physiological information.

31. The method according to claim 19, wherein the step of providing virtual assistance comprises providing a message to the user, the message selected from the group of messages consisting of: a textual message, a voice recorded message, a video message, an audio message, a pictorial message, or an email.

32. A non-transitory computer readable media having stored thereon processor-executable software instructions configured to cause a processor to perform operations for automatically providing virtual assistant to a user based on physiological information of the user, the operations comprising:
receiving user input data comprising diet information;
receiving physiological information of the user;
transmitting the user input data and physiological information of the user to a control processor and rules engine;
determining by the control processor and rules engine whether a combination of the physiological information and user input data identify a trend;
determining whether virtual assistance was previously provided based on the trend;
if it is determined that the trend exists, automatically providing the user with virtual assistance from the control processor and rules engine based on the trend; and
if it is determined previous virtual assistance was provided, providing different virtual assistance that takes into account previous virtual assistance, the trend, and the user input data.

33. The non-transitory computer readable media of claim 32, wherein the trend is a detrimental trend and the virtual assistance is to counter the detrimental trend.

34. The non-transitory computer readable media of claim 32, wherein the trend is a beneficial trend and the virtual assistance is to promote the beneficial trend.

35. A method for identifying patterns in physiological information of the user, the method comprising the steps of:
- obtaining user input data comprising diet information;
- obtaining physiological information of the user with an electronic medical device;
- transmitting the obtaining user input data and the obtained physiological information of the user to a control processor and rules engine;
- storing the physiological information in a memory unit for at least a selected period of time;
- analyzing the physiological information over the selected period of time to determine whether at least one pattern exists;
- determining whether virtual assistance was previously provided relating to the at least one pattern; and
- providing virtual assistance to the user relating to the at least one pattern, wherein the virtual assistance takes into account any previously provided virtual assistance, the physiological information and the user input data.

36. The method according to claim 35, wherein the selected period is selected from a group consisting of: minutes, hours, days, weeks, months, or years.

37. The method according to claim 35, further comprising the step of correlating the at least one pattern with at least one event.

38. The method according to claim 37, wherein the provided virtual assistance further relates to the correlated event.

39. The method according to claim 37, wherein the at least one event relates to an input selected from the group of inputs consisting of:
- the physiological information and other relevant information.

40. The method according to claim 39, wherein the relevant information consists of information entered by the user.

41. The method according to claim 40, wherein the information manually entered by the user comprises at least one of dietary information, physical activity information, and medication information.

42. The method according to claim 35, further comprising the step of alerting at least one of the user, medical personnel, or a care giver, when the pattern is not correlated to an event.

43. A system for providing virtual assistance to a user when a trend in physiological information is detected, the system comprising:
- a remote station configured to be carried by a user;
- an electronic medical device to sense physiological information about the user, the electronic medical device coupled to the remote station;
- a memory, the memory coupled to the remote station to store user input data and physiological information over at least a selected time period;
- a pattern recognition engine connected to the memory, the pattern recognition engine being configured to analyze the stored user input data and physiological information over at least the selected time period to determine whether a pattern exists;
- a control processor coupled to the memory and pattern recognition engine configured to determine whether a tip based on the detected pattern has been previously generated; and
- a rules engine, the rules engine connected to the pattern recognition engine and control processor such that when the pattern recognition engine determines the pattern exists, the rules engine generates the tip based on the detected pattern, user input data, and any previously generated tip, wherein the user input data comprises diet information.

44. The system of claim 43 wherein the rules engine only generates the tip when the detected pattern is an unexpected pattern.

45. The system of claim 44, further comprising a user interface coupled to at least one of the remote station or the electronic medical device to receive relevant information from the user about the physiological information.

46. The system of claim 45, wherein the relevant information comprises at least one of dietary information, medication information, and physical activity information.

47. The system of claim 45, further comprising a correlation engine, the correlation engine connected to the pattern recognition engine to determine whether a correlation between the defected pattern and the relevant information exists.

48. The system of claim 47, wherein the tip also is based on the correlation between the detected pattern and the relevant information.

49. A non-transitory computer readable media having stored thereon processor-executable software instructions configured to cause a processor to perform operations for providing virtual assistance to a user when a trend in physiological information is detected, the operations comprising:
- receiving user input data comprising diet information;
- receiving physiological information about a user;
- storing the received physiological information for at least a selected period of time;
- analyzing the received user input data and physiological information over at least the selected period of time to determine whether a pattern exists; and
- determining whether a tip based on the determined pattern was previously generated; and
- generating the tip for the user based on the determined pattern, wherein the generation of the tip takes into account any previously generated tips, the user input data and the pattern, wherein the user input data comprises diet information.

* * * * *